United States Patent [19]

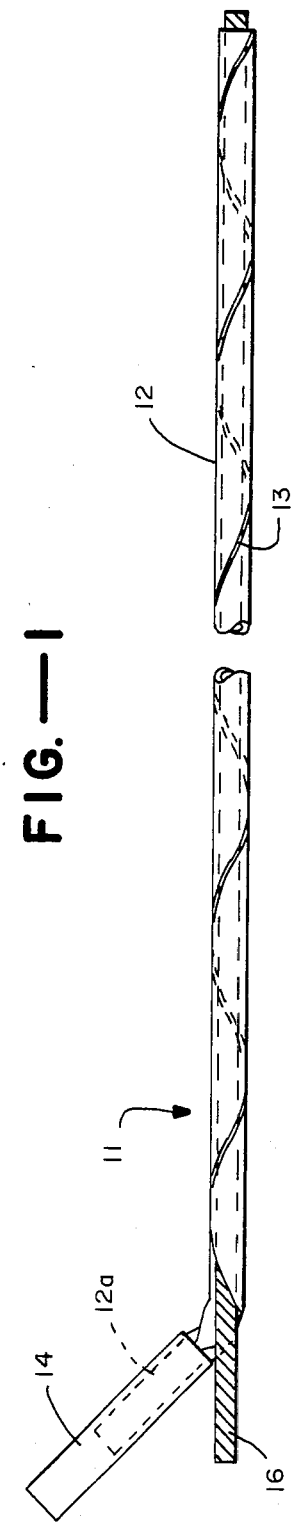
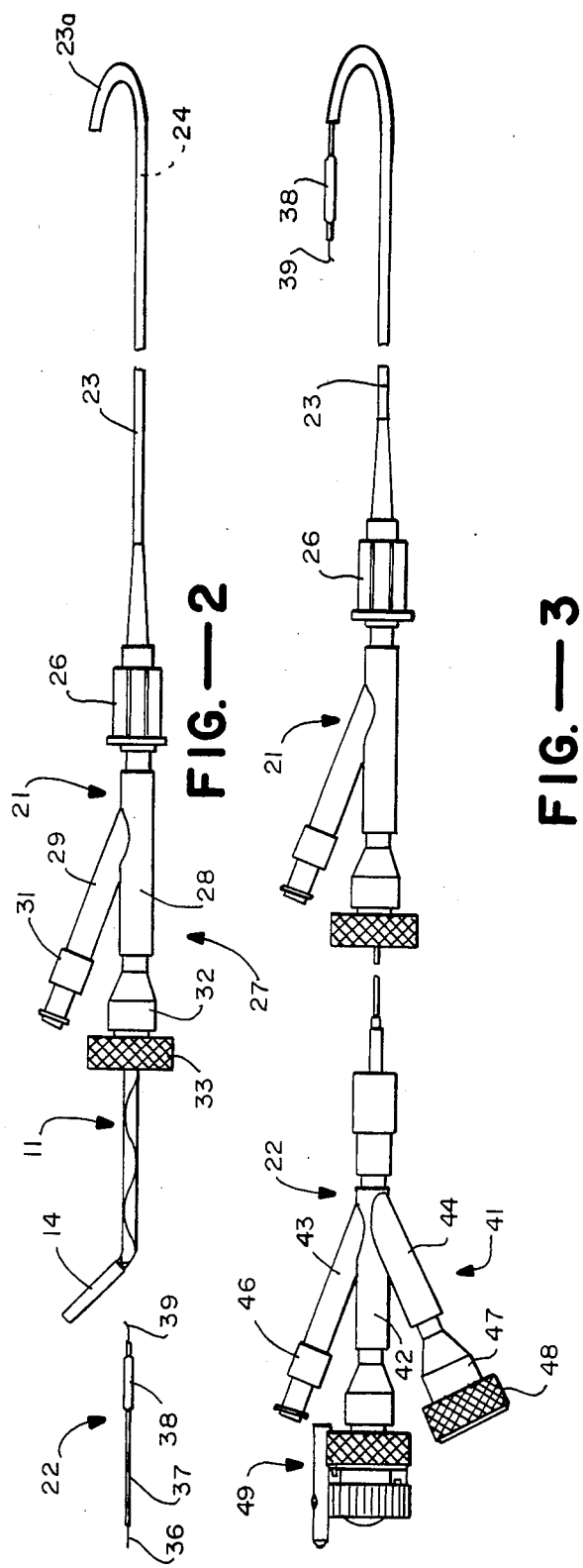

Frisbie

[11] Patent Number: 4,569,347
[45] Date of Patent: Feb. 11, 1986

[54] CATHETER INTRODUCING DEVICE, ASSEMBLY AND METHOD

[75] Inventor: Jeffrey S. Frisbie, San Jose, Calif.

[73] Assignee: Advanced Cardiovascular Systems, Inc., Mountain View, Calif.

[21] Appl. No.: 615,142

[22] Filed: May 30, 1984

[51] Int. Cl.[4] .............................................. A61M 29/02
[52] U.S. Cl. .................................. 128/344; 604/164; 604/165; 604/171
[58] Field of Search ............... 128/344, 343, 657, 772; 604/95, 96, 97, 98, 164, 165, 171, 99, 100, 101, 102

[56] References Cited

U.S. PATENT DOCUMENTS

| | | | |
|---|---|---|---|
| 4,175,564 | 11/1979 | Kwak | 604/171 |
| 4,367,747 | 1/1983 | Witzel | 604/101 |
| 4,412,832 | 11/1983 | Kling et al. | 604/164 |
| 4,501,580 | 2/1985 | Glassman | 604/102 |

FOREIGN PATENT DOCUMENTS 512456  9/1939  United Kingdom ............... 128/344

*Primary Examiner*—Gene Mancene
*Assistant Examiner*—Cary E. Stone

[57] ABSTRACT

Catheter introducing device for inserting a dilatation catheter into a guiding catheter having a flexible tubular member formed of a flexible material. The tubular member has a spiral cut extending longitudinally throughout the entire length of the tubular member. A pull member is secured to the tubular member to facilitate removal of the device after it has been utilized for introducing the dilatation catheter into the guiding catheter.

8 Claims, 3 Drawing Figures

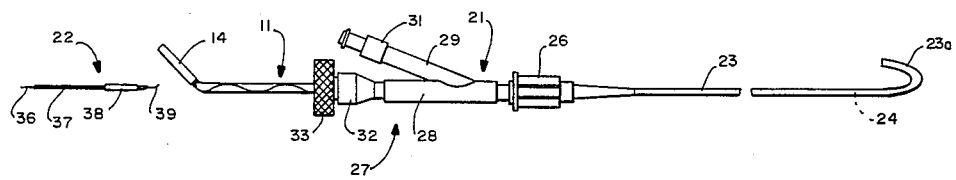

CATHETER INTRODUCING DEVICE, ASSEMBLY AND METHOD

This invention relates to a catheter introducing device which can be utilized for introducing an additional catheter such as a dilatation catheter into a guiding catheter, an assembly utilizing the same and a method.

Guiding catheters and dilatation catheters have heretofore been provided. Typical of such catheters are those described in U.S. Pat. No. 4,323,071. In addition there has been developed what is called a low profile dilatation catheter such as disclosed in application Ser. No. 522,835 filed Aug. 12, 1983. These low profile dilatation catheters have flexible tips which often are bent in predetermined configurations as determined by the physician before insertion of the same into the guiding catheter. It has been found that guiding catheters typically may be provided with a rotating hemostatic valve. In attempting to thread a dilatation catheter through a guiding catheter, it has very often been found to be difficult, if not impossible, to thread the flexible tip of the dilatation catheter through and past the rotating hemostatic valve forming a part of the guiding catheter without impairing the predetermined bend in the tip. There is therefore a need for a device and method which facilitates negotiating the dilatation catheter past the rotating hemostatic valve during insertion of the dilatation catheter into the guiding catheter.

In general it is an object of the present invention to provide a catheter introducing device facilitating introduction of the dilatation catheter into a guiding catheter.

Another object of the invention is to provide a catheter introduction device of the above character in which the device can be readily removed after the dilatation catheter has been inserted into the guiding catheter.

Another object of the invention is to provide a catheter introducing device of the above character which is relatively simple and easy to manufacture.

Another object of the invention is to provide the catheter introducing device and a method for using the same which is relatively simple and which can be readily understood by the user.

Additional features and objects of the invention will appear from the following description in which the preferred embodiment is set forth in detail in conjunction with the accompanying drawings.

FIG. 1 is a side elevational view of a catheter introducing device incorporating the present invention with a mandrel disposed therein.

FIG. 2 is a side elevational view of a portion of a guiding catheter assembly showing the catheter introducing device disposed in the same and being in a position to accept a dilatation catheter of the type shown in FIG. 3.

FIG. 3 is a side elevational view of a guiding catheter assembly with a dilatation catheter assembly disposed in the same after utilization of the catheter introducing device of the present invention and with the catheter introducing device removed.

In general the catheter introducing device is used for inserting a dilatation catheter into a guiding catheter and consists of a flexible tubular member formed of a flexible material. The tubular member has a helical or spiral cut extending longitudinally throughout the entire length of the tubular member. A pull member adapted to be grasped by the human hand is secured to the tubular member at one end thereof to facilitate removal of the catheter introducing device after it has been utilized for introducing the dilatation catheter into the guiding catheter.

More particularly as shown in FIG. 1 of the drawings, the catheter introducing device 11 consists of a flexible hollow tubular member 12. The tubular member 12 is formed of a suitable material such as a medical grade plastic. For example, it can be formed of a high or a low densith polyethylene as well as other plastic materials such as Teflon.

The tubular member 12 can have suitable inside and outside diameters. For example, the inside diameter can be 0.046 inches with an outside diameter of 0.056 inches with a wall thickness of 0.005 inches. The tubular member 12 also can have a suitable length such as four inches.

A helical or spiral cut 13 is provided in the tubular member and extends the entire length of the tubular member. The helical or spiral cut can have any desired pitch, for example, the spirals can have a density ranging from 2 to 3 spirals per inch of length of the tubular member. The helical or spiral cut 13 can be formed in any conventional manner. For example, the tubular member 12 can be placed on a mandrel and the mandrel positioned in a fixture to rotate the same. The tubular member or the cutting blade can be moved longitudinally with respect to each other during the time that rotation is taking place to form the spiral cut.

A pull member 14 is provided on one end of the tubular member 12 and can take any suitable form. For example, as shown in FIG. 1, the pull member 14 is formed by taking a small length as, for example, one inch of polyethylene shrink tubing of a type well known to those skilled in the art. An end portion 12a of the tubular member 12 is unwrapped along the spiral cut 13 which has been formed and is inserted into the shrink tubing 14. The shrink tubing is then heated to cause it to shrink onto the portion 12a. At the same time the heat softens the portion 12a of the tubular member 12 while it is maintained at a suitable angle as, for example, the approximately 45° angle shown in FIG. 1. The portion 12a is retained at this angle during cooling of the shrink tubing so that a permanent set is introduced in the portion 12a. The shrink tubing because of its shrink characteristics upon heating is permanently affixed to the portion 12a and serves as the pull member 14 which is utilized as hereinafter described in utilization of the catheter introducing device 11.

The catheter introducing device 11 is shown disposed in a guiding catheter assembly 21 ready to be used for facilitating insertion of a dilatation catheter assembly 22 into the guiding catheter assembly 21. The guiding catheter assembly 21 is of a conventional type with one of its early progenitors being disclosed in U.S. Pat. No. 4,323,071. It consists generally of a guiding catheter 23 which is provided with a guiding passageway 24 extending the length thereof. As can be seen, the guiding catheter 23 is provided with a conventional bend 23a at its distal extremity. A conventional rotating hemostatic valve 26 is secured to the proximal end of the guiding catheter 23. A Y-adapter 27 is mounted on the hemostatic valve 26. The Y-adapter is provided with a center or main arm 28 and a side arm 29. A conventional Leur fitting 31 is provided on the side arm 29. The side arm 29 is conventionally used for introduction of a radiographic contrast dye. The center arm 28 which extends axially of the guiding catheter 23 is provided with an O-ring fitting 32 of a conventional type which can be compressed by the rotation of a knurled knob 33.

The dilatation catheter assembly 22 also is of a conventional type. For example, it can be of the type described in copending application Ser. No. 322,835 filed Aug. 12, 1983. As described therein, it consists of the flexible guide wire 36 upon which there is mounted a tubular member 37. A balloon 38 capable of being inflated is provided on the tubular member and has its distal extremity sealed with respect to the guide wire 36. A flexible bendable tip 39 is provided at the distal extremity of the guide wire 36. A triple arm adapter 41 is mounted on the proximal extremity of the tubular member 37 and is provided with a central arm 42 and side arms 43 and 44. A Luer fitting 46 of a conventional type is provided on the side arm 42. A compression type fitting 47 which is provided with an O-ring (not shown) and a knurled knob 48 is provided on the side arm 44. A rotation assembly 49 is provided for providing limited rotation of the guide wire 36 and the tip 39 provided on the same and is described in detail in copending application Ser. No. 615,118 filed 5/30/84. The rotation assembly 49 is provided on the central or main arm 42 which is disposed axially of the tubular member 37.

Operation and use of the catheter introducing device may now be briefly described as follows. Let it be assumed that the guiding catheter 21 has been inserted into an arterial vessel leading into the heart and that it is now desired to insert a dilatation catheter 22 into the guiding catheter. This is readily accomplished by taking the catheter introducing device 11 with the mandrel 16 therein and positioning it in the center arm or leg 28 of the triple arm adapter 41 so that the distal extremity of the catheter introducing device 11 extends beyond the hemostatic valve 26. The mandrel 16 can then be removed. The dilatation catheter 22 which the physician wishes to insert into the guiding catheter has had its tip 39 bent in the desired conformation as shown. The tip of the dilatation catheter then can be inserted into the catheter introducing device 11. Alternatively, prior to introducing device 11 into center arm 28, mandrel 16 can be removed, device 11 passed over tip 39 and balloon 38, and the assembly thus formed introduced through center arm 28 and past valve 26. It has been found that the dilatation catheter can be readily threaded through the relatively smooth inner surface provided by the interior of the tubular member 12 so that it readily clears the hemostatic valve 26 and thereafter enters the guiding catheter 23 and extends the length of the same until the balloon 38 and the tip 39 extend out of the guiding catheter as shown in FIG. 3.

As soon as the dilatation catheter has been inserted into the guiding catheter past the hemostatic valve 26, the catheter introducing device 11 can be removed. This can be readily accomplished by holding the dilatation catheter 22 in position with one hand and utilizing the other hand to grasp the pull member or tab 14 of the catheter introducing device and pulling it outwardly generally axially of the guiding catheter. As the catheter introducing device 11 is withdrawn, the spiral cut provided in the tubular member 12 permits the tubular member to gradually unwrap or unravel from around the dilatation catheter in a progressive spiral manner until the catheter introducing device 11 has been completely separated from the dilatation catheter 11. After the catheter introducing device 11 has been removed, the mandrel 16 can be reinserted therein and the device is again ready for the next use of the device 11. Also, by removing device 11 from catheter 22, capability of radiographic contrast injection through side port 29 is maintained, and the entire usable length of catheter 22 is retained.

It can be seen that the catheter introducing device can be readily used by the physicians to facilitate introduction of the dilatation catheter into the guiding catheter. This is particularly important in that it makes it possible to insert the dilatation catheter into the grinding catheter while retaining the desired bend in the tip 39. The catheter introducing device is constructed in such a manner so that it can be readily manufactured.

What is claimed is:

1. In a catheter introducing device for inserting a dilatation catheter into a guiding catheter, a flexible tubular member formed of a flexible material, the tubular member having a spiral cut extending longitudinally throughout the entire length of the tubular member, a pull member secured to the tubular member to facilitate removal of the device after it has been utilized for introducing the dilatation catheter into the guiding catheter.

2. A device as in claim 1 together with a mandrel disposed in the tubular member and serving to retain the shape of the tubular member when the device is not in use.

3. A catheter introducing device as in claim 1 wherein said flexible material is formed of a medical grade plastic and wherein said pull member is formed of plastic and is secured to the tubular member.

4. A device as in claim 3 wherein said pull member extends at an angle of approximately 45° from the longitudinal axis of the tubular member.

5. A device as in claim 4 wherein said pull member is formed of a heat shrinkable plastic and is bonded to a portion of said tubular member.

6. In an assembly of the character described, a guiding catheter having a guiding passageway extending therethrough, a fitting assembly carried by the proximal extremity of the guiding catheter, a dilatation catheter adapted to be inserted into the guiding passageway of the guiding catheter, a catheter introducing device disposed in the proximal extremity of the guiding catheter and extending out of the fitting, said catheter introducing device including a flexible tubular member formed of a flexible material, the tubular member having a spiral cut extending longitudinally throughout the entire length thereof and a pull member secured to said tubular member at one end thereof, said dilatation catheter extending through said catheter introducing device and into the guiding catheter, said catheter introducing device being removable by grasping on the pull member and pulling the same out of the passageway of the guiding catheter while said dilatation catheter remains in said passageway in the guiding catheter.

7. An assembly as in claim 6 wherein said pull member extends at an angle with respect to the longitudinal axis of the tubular member.

8. In a method for introducing a dilatation catheter into a guiding catheter by the use of a catheter introducing device having a tubular member with a spiral cut extending longitudinally throughout the length of the same, inserting the guiding catheter into the blood vessel, inserting the catheter introducing device into the proximal extremity of the guiding catheter and introducing the dilatation catheter into the catheter introduction device so that it extends into the guiding catheter, removing the catheter guiding device by causing the same to unravel about the dilatation cathether while the dilatation catheter remains in place in the guiding catheter.

* * * * *